United States Patent

Leppard et al.

Patent Number: 5,274,170
Date of Patent: Dec. 28, 1993

[54] SUBSTITUTED BENZOPHENONE STABILIZERS

[75] Inventors: David G. Leppard, Marly, Switzerland; David H. Steinberg, Bronx, N.Y.; Henri Dubas, Marly, Switzerland

[73] Assignee: Ciba-Geigy Corporation, Ardsley, N.Y.

[21] Appl. No.: 898,656

[22] Filed: Jun. 15, 1992

Related U.S. Application Data

[62] Division of Ser. No. 699,102, May 13, 1991, Pat. No. 5,145,766.

[30] Foreign Application Priority Data

May 16, 1990 [CH] Switzerland .................. 1653/90

[51] Int. Cl.$^5$ .................. C07C 69/76; C07C 309/73
[52] U.S. Cl. .................. 560/75; 560/67; 560/61; 560/193; 554/220; 554/229
[58] Field of Search .................. 560/75

[56] References Cited

U.S. PATENT DOCUMENTS

| | | | |
|---|---|---|---|
| 4,252,893 | 2/1981 | Iwamuro et al. | 560/75 |
| 4,573,062 | 2/1986 | Satake et al. | 560/75 |
| 4,661,440 | 4/1987 | Tschopp et al. | 560/75 |
| 4,906,559 | 3/1990 | Nishijima et al. | 560/75 |
| 5,006,453 | 4/1991 | Takahashi et al. | 560/75 |

FOREIGN PATENT DOCUMENTS 1067852 4/1986 Japan .
2022274 12/1979 United Kingdom .

OTHER PUBLICATIONS

Chemical Abstracts CA 83 (8):60222x 1975.
Y. I. Yemchin et al., Mater. Plast. Elastomer, Jan. 1985, pp. 41–44.

Primary Examiner—Paul J. Killos
Attorney, Agent, or Firm—Luther A. R. Hall

[57] ABSTRACT

Compounds of the formula

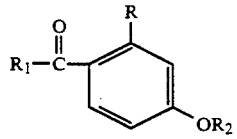

in which R is hydrogen or hydroxyl, $R_1$ is alkyl, alkoxy, amino or aryl, and $R_2$ is hydrocarbylcarbonyl or hydrocarbylsulfonyl, are highly suitable for stabilizing magenta couplers in photographic materials.

4 Claims, No Drawings

SUBSTITUTED BENZOPHENONE STABILIZERS

This is a divisional of application Ser. No. 07/699,102, filed on May 13, 1991, now U.S. Pat. No. 5,145,766, issued on Sep. 8, 1992.

The present invention relates to a process for stabilising magenta couplers and the corresponding image dyes in photographic materials using compounds containing benzoyl groups.

Image dyes in virtually all photographic images undergo changes in the course of time due to the action of atmospheric oxygen, moisture, heat and light which are evident from colour shifts and losses in contrast and colour density. This is particularly true of images obtained after chromogenic development and specifically of images which still contain coupler molecules even after processing. In these images, not only bleaching of the image dyes, but also undesired yellowing of image whites and formation of dyes by reaction of these coupler molecules with, for example, image dyes and with themselves, are observed. The various rates of these reactions for yellow, cyan and magenta couplers result in said colour shifts and losses in contrast in the images.

The undesired yellowing of pale image areas and colour-formation reactions of the coupler molecules proceed both in the light and in the dark. Stabilisation of photographic images is thus of particular importance.

In particular, high stability of photographic images in the dark is required by institutions such as museums, archives, agencies and galleries, which must be interested in the preservation of the original image dyes.

In this context, Japanese Published Application 52/082 219 proposes improving the stability of photographic images in the dark by using polyvinylimidazoles. For the same purpose, Japanese Published Application 53/108 428 employs substituted 4-hydroxyphosphoranilides. Pyrocatechol diethyl ether and dibenzoxaphosphorins are described in Japanese Published Application 57/204 036 and U.S. Pat. No. 4,661,440 respectively as stabilisers for storage of photographic images in the dark.

It has now been found that certain compounds containing benzoyl groups can provide photographic materials with good stability in the dark by stabilising the magenta couplers these materials contain. "Photographic materials" below is taken to mean both unexposed materials containing magenta couplers and photographic images produced therefrom, since the compounds used according to the invention are present in the layers of the unexposed materials and already develop their stabilising effect therein.

The present invention accordingly relates to a process for stabilising magenta couplers and corresponding image dyes in photographic materials, which comprises incorporating at least one compound of the formula

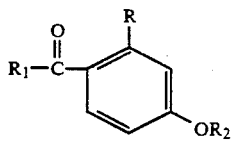
(1)

in which R is hydrogen or hydroxyl, $R_1$ is alkyl or alkoxy, in each case having 1 to 18 carbon atoms, $-NR_4R_5$ in which $R_4$ and $R_5$, independently of one another, are hydrogen or alkyl having 1 to 18 carbon atoms, or $R_1$ is a radical of the formula

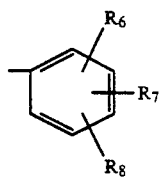

in which $R_6$, $R_7$ and $R_8$, independently of one another, are hydrogen, hydroxyl or alkyl, in each case having 1 to 8 carbon atoms, or $R_1$ is a radical of the formula

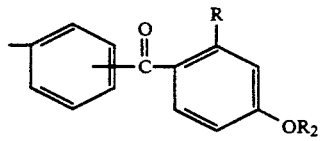

in which R is as defined above, and $R_2$ is $-COR_{11}$ or $-SO_2R_{11}$ in which $R_{11}$ is alkyl having 1 to 18 carbon atoms, alkenyl having 2 to 18 carbon atoms, phenylalkyl having 1 to 4 carbon atoms in the alkyl moiety or a radical of the formula

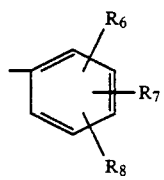

in which $R_6$, $R_7$ and $R_8$ are as defined above, or $R_2$ is $-COCO_2R_{10}$ or $-CO_2R_{10}$ in which $R_{10}$ is as defined above, or $R_2$ is a radical of the formula

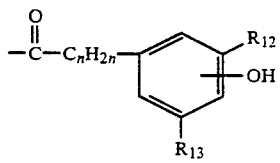

or

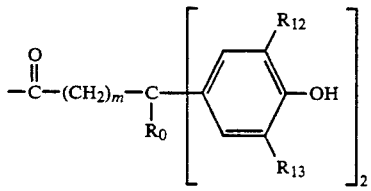

in which m is 1 to 6, and $R_0$ is hydrogen or methyl, and n is 0 to 14, and $R_{12}$ and $R_{13}$, independently of one another, are hydrogen, alkyl, in each case having 1 to 8 carbon atoms, cyclopentyl, cyclohexyl, alkylphenyl having 1 to 8 carbon atoms in the alkyl moiety, or phenyl, into the layer containing the magenta couplers or into a layer adjacent thereto.

The present invention furthermore relates to the photographic material stabilised according to the invention, to the novel compounds of the formula (1a), and to a process for stabilising magenta couplers and the corresponding image dyes using the compounds of the formula (1).

In the compounds of the formula (1), the substituent R in the ortho-position to the carbonyl group may be hydrogen or hydroxyl.

$R_1$ may be alkyl having 1 to 18 carbon atoms, for example methyl, ethyl, propyl, butyl, pentyl, hexyl, heptyl, octyl, nonyl, undecyl, dodecyl, hexadecyl or octadecyl, or a corresponding branched isomer. Furthermore, $R_1$ may be alkoxy having 1 to 18 carbon atoms. Suitable examples of alkoxy radicals $R_1$ are those in the above list. $R_1$ may furthermore be an amino group of the formula $-NR_4R_5$ where $R_4$ and $R_5$, independently of one another, are hydrogen or alkyl having 1 to 18 carbon atoms. Suitable alkyl radicals are given above. $R_1$ may alternatively be one of the following aromatic systems of the formula

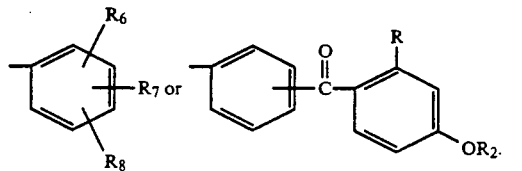

In these formulae, the substituents $R_6$, $R_7$ and $R_8$, independently of one another, are hydrogen, hydroxyl or alkyl having 1 to 8 carbon atoms, such as methyl, propyl, butyl, hexyl or octyl, or a corresponding branched isomer. Substituent R is as defined above. Suitable radicals for the substituent $R_2$ are those of the formulae $-COR_{11}$, $-SO_2R_{11}$, $-COCO_2R_{10}$, $-CO_2R_{10}$,

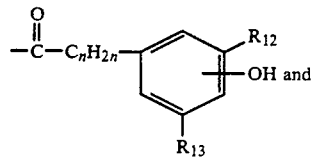

and

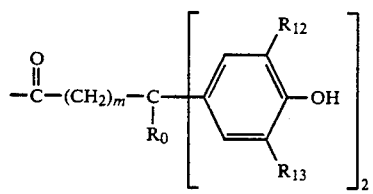

in which $R_{11}$ is alkyl or alkenyl having 1 or 2 to 18 carbon atoms (see above), furthermore phenylalkyl having 1 to 4 carbon atoms in the alkyl moiety (see above) or a radical of the formula

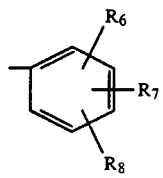

in which $R_6$, $R_7$ and $R_8$ are as defined above, $R_{10}$ is as defined above, the substituents $R_{12}$ and $R_{13}$, independently of one another, are hydrogen, alkyl in each case having 1 to 8 carbon atoms (see above), cyclopentyl, cyclohexyl, alkylphenyl in each case having 1 to 8 carbon atoms in the alkyl moiety (see above) or phenyl, $R_0$ is hydrogen or methyl, n is an integer from 0 to 14, and m is from 1 to 6.

In a group of preferred compounds of the formula (1), $R_1$ is alkyl or alkoxy in each case having 1 to 18 carbon atoms, or a radical of the formula

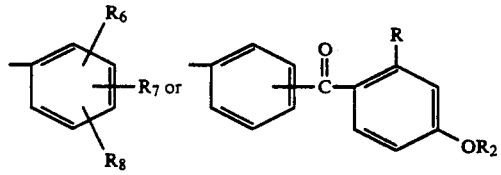

in which R, $R_2$, $R_3$, $R_6$, $R_7$ and $R_8$ are as defined above. $R_1$ is in particular alkyl or alkoxy in each case having 1 to 8 carbon atoms or a radical of the formula

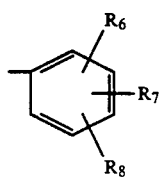

in which $R_6$, $R_7$ and $R_8$, independently of one another, are hydrogen, hydroxyl or alkyl having 1 to 4 carbon atoms, R is hydroxyl and $R_2$ is $-COR_{11}$ in which $R_{11}$ is alkyl having 1 to 18 carbon atoms, or is a radical of the formula

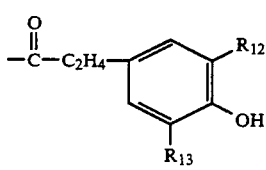

in which $R_{12}$ and $R_{13}$, independently of one another, are hydrogen or alkyl having 1 to 4 carbon atoms.

Of these, particular preference is given to those compounds in which $R_1$ is alkyl or alkoxy in each case having 1 to 4 carbon atoms, or is a radical of the formula

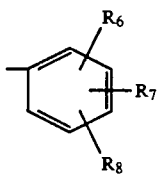

in which $R_6$, $R_7$ and $R_8$, independently of one another, are hydrogen, hydroxyl or alkyl having 1 to 4 carbon atoms, and $R_2$ is $-COR_{11}$ in which $R_{11}$ is alkyl having 12 to 18 carbon atoms, or a radical of the formula

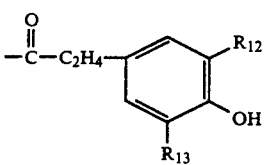

in which $R_{12}$ and $R_{13}$ are alkyl in each case having 1 to 4 carbon atoms.
Specific examples of the compounds of the formula (1) are the compounds of the formulae (2) to (33):
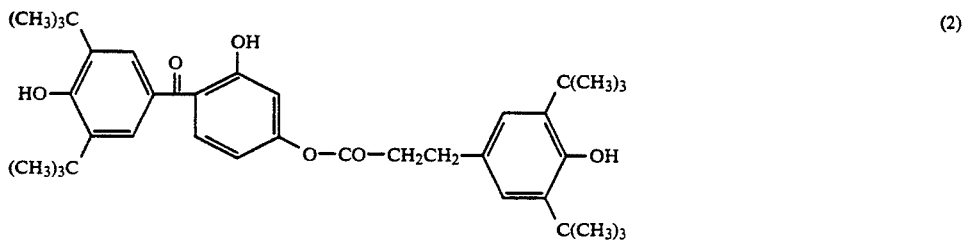
(2)
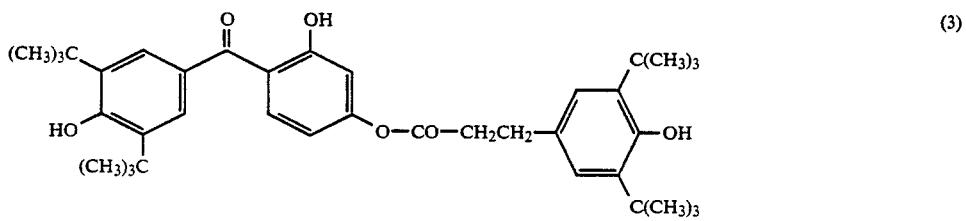
(3)
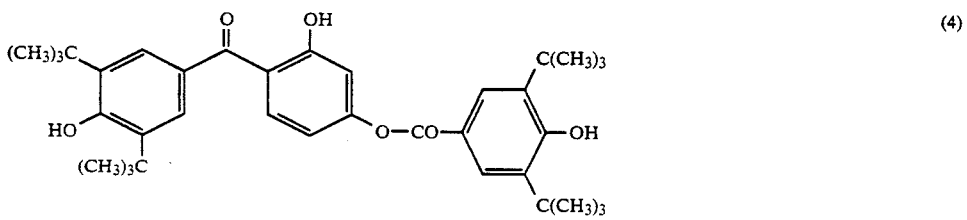
(4)
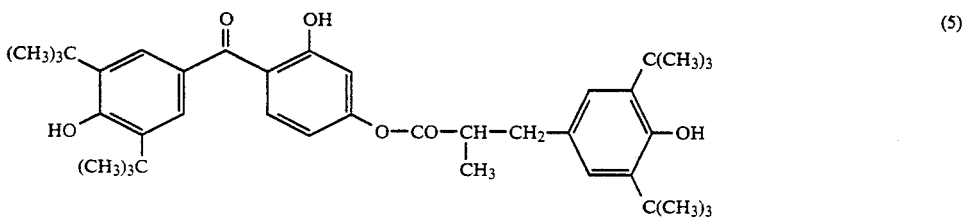
(5)
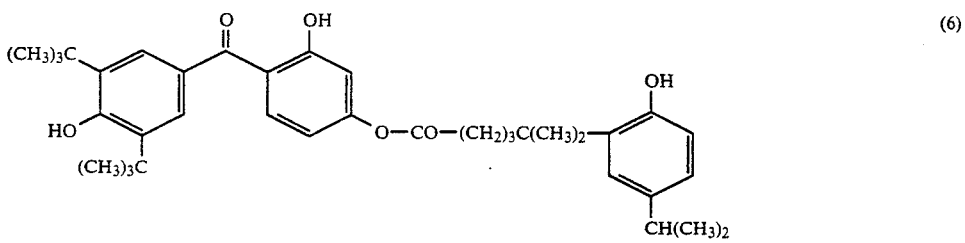
(6)
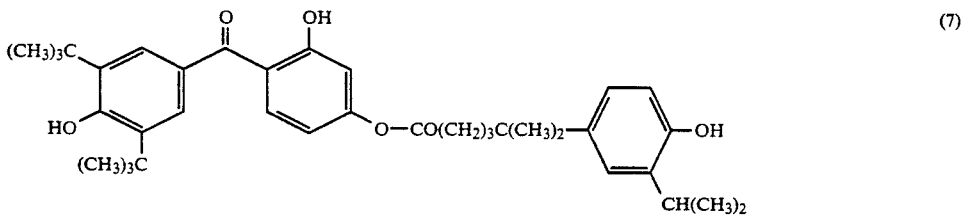
(7)
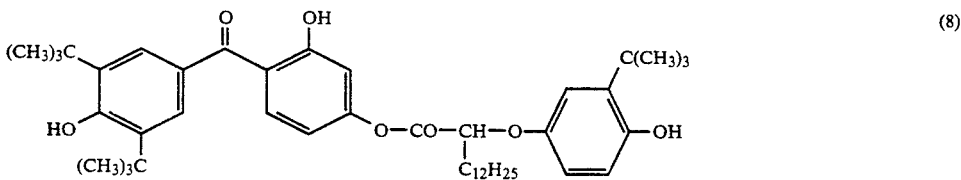
(8)

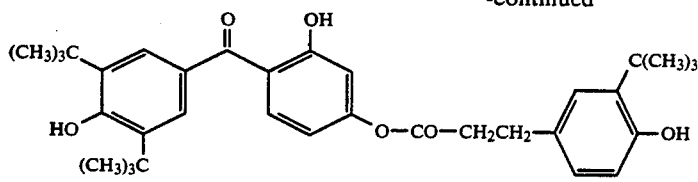
(9)
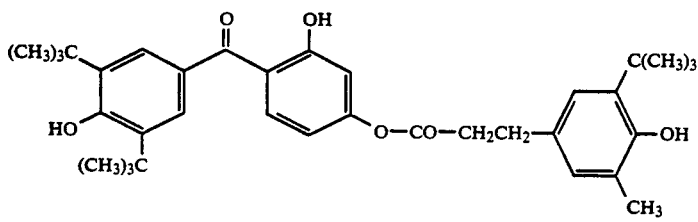
(10)
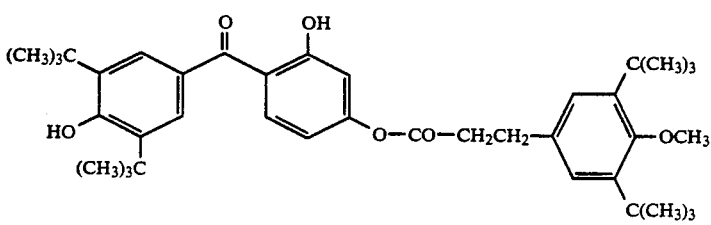
(11)
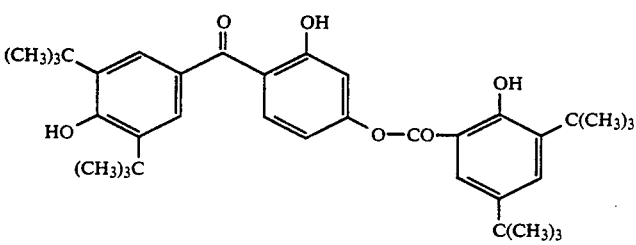
(12)
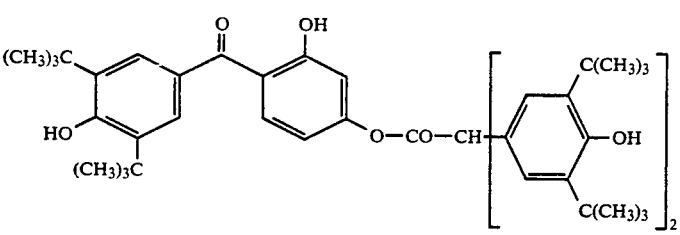
(13)
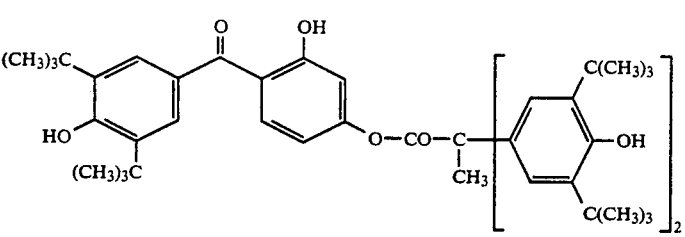
(14)
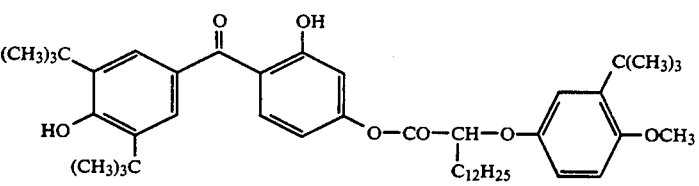
(15)
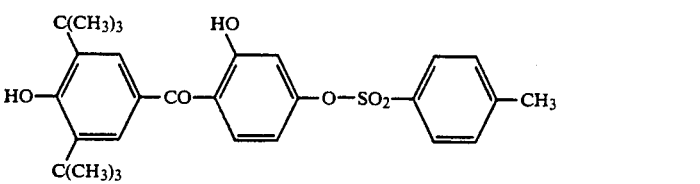
(16)

-continued
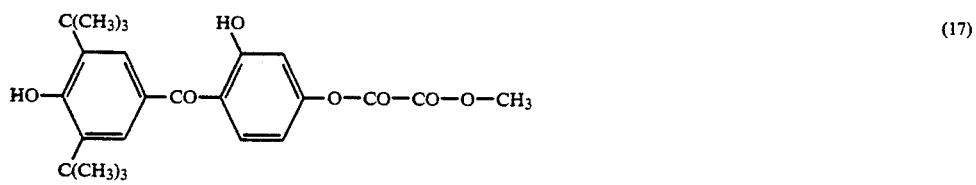 (17)
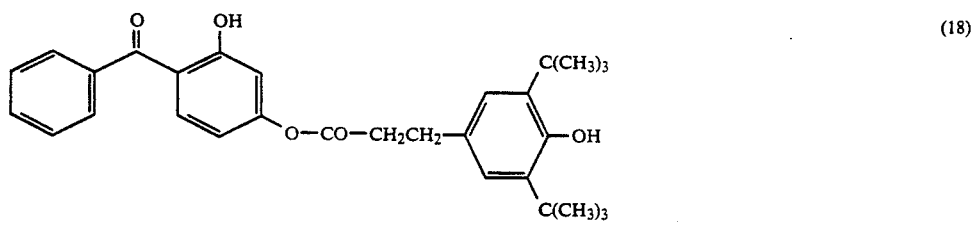 (18)
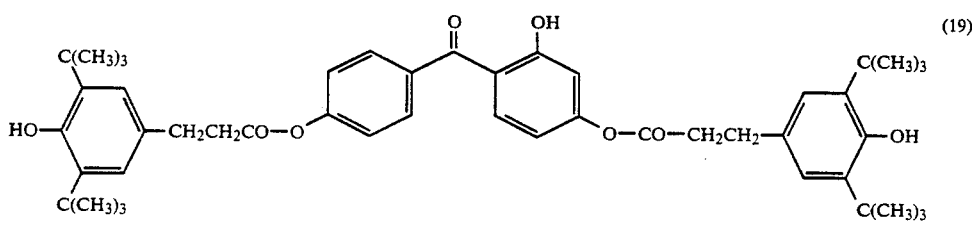 (19)
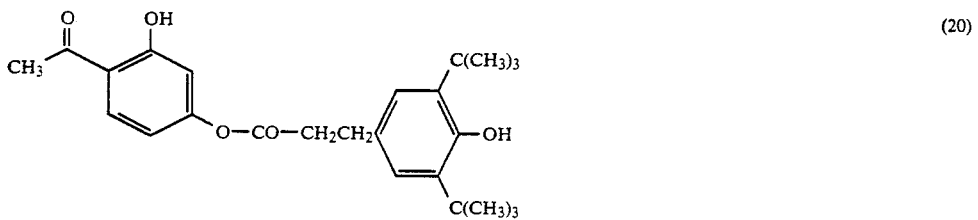 (20)
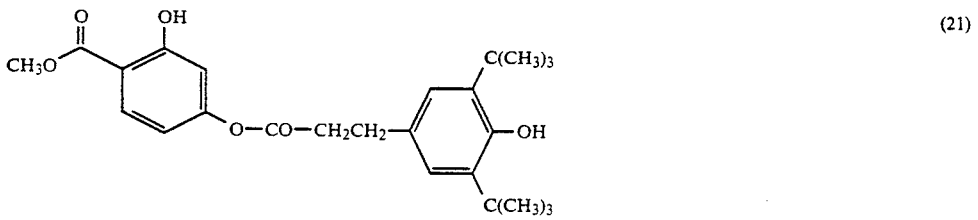 (21)
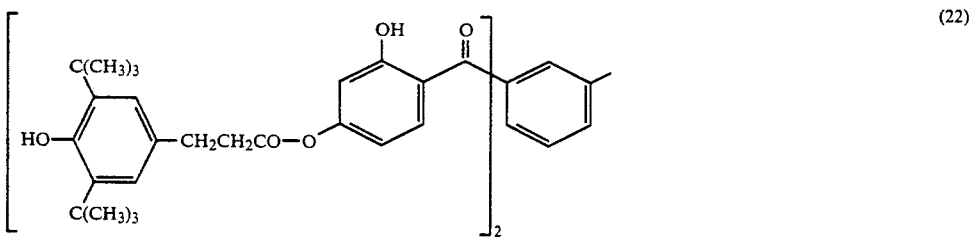 (22)
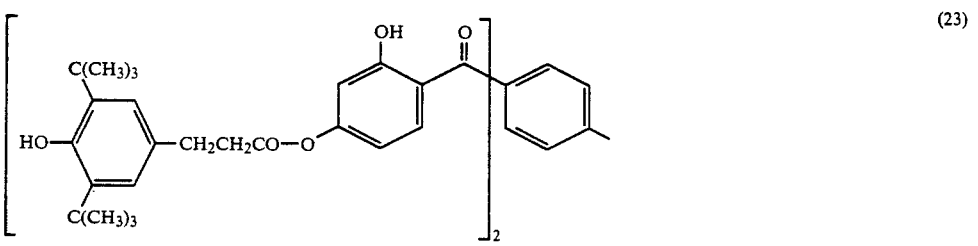 (23)

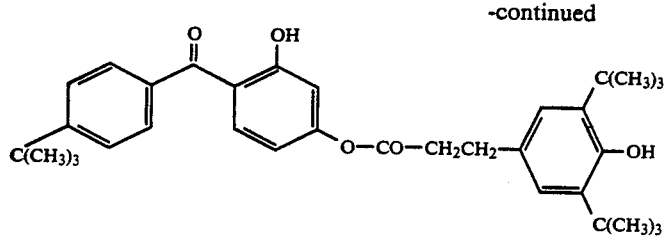 (24)
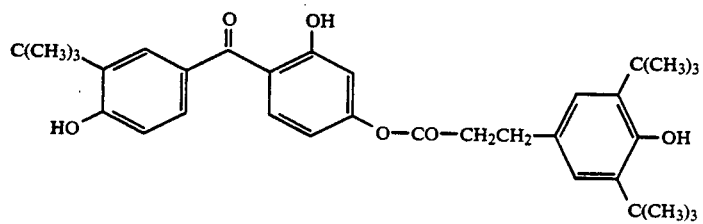 (25)
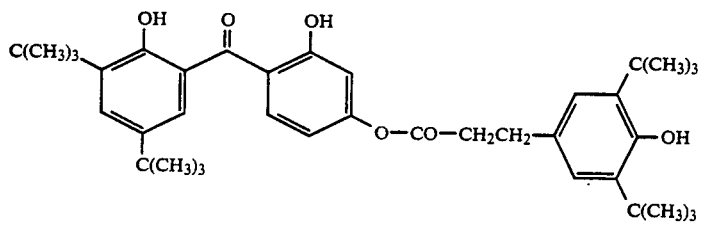 (26)
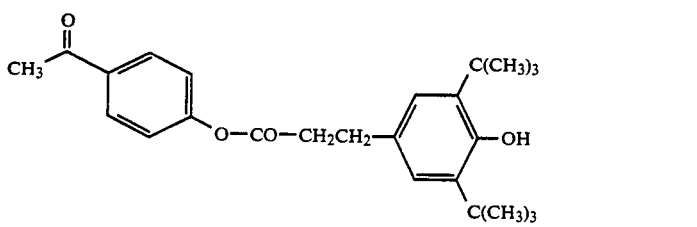 (27)
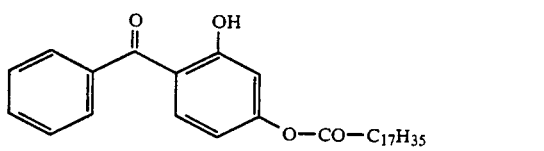 (28)
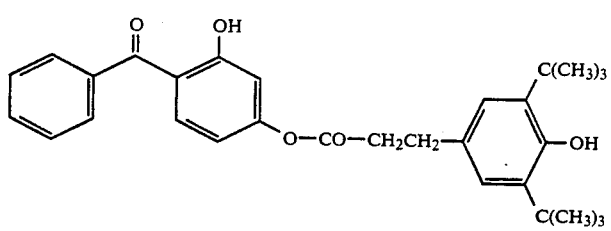 (29)
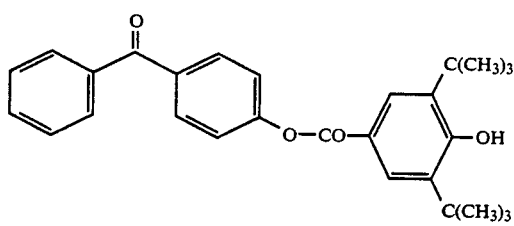 (30)
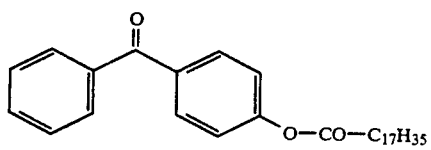 (31)

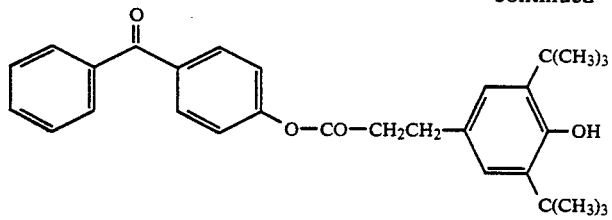

(32)

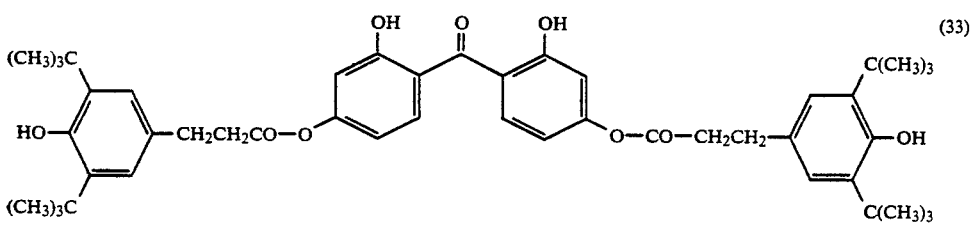

(33)

The compounds of the formula (1) can be used to stabilise virtually any type of magenta coupler in photographic materials. These magenta couplers may be, for example, simple 1-aryl-5-pyrazolones or pyrazole derivatives fused to 5-membered hetero rings, for example imidazopyrazoles, pyrazolotriazoles or pyrazolotetrazoles.

One group of magenta couplers comprises 5-pyrazolones of the formula

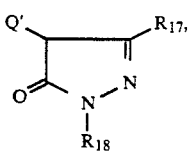

(A)

as described in British Patent 2 003 473. In this formula, $R_{17}$ is hydrogen, alkyl, aryl, alkenyl or a heterocyclic group, $R_{18}$ is hydrogen, alkyl, aryl, a heterocyclic group, an ester group, alkoxy group, alkylthio group, carboxyl group, arylamino group, acylamino group, (thio)urea group, (thio)carbamoyl group, guanidino group or sulfonamido group, and Q' is a leaving group.

Typical examples of magenta couplers of this type are compounds of the formula

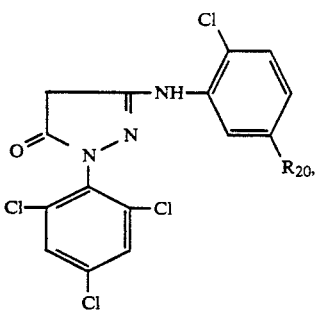

(B)

in which $R_{20}$ is hydrogen, alkyl, acylamino, carbamoyl, sulfamoyl, sulfonamide, alkoxycarbonyl, acyloxy or a urethane group.

Further examples of tetraequivalent magenta couplers of this type are given in U.S. Pat. Nos. 2,983,608; 3,061,432; 3,062,653; 3,127,269; 3,152,896; 3,311,476; 3,419,391; 3,519,429; 3,558,319; 3,582,322; 3,615,506; 3,684,514; 3,834,908; 3,888,680; 3,891,445; 3,907,571; 3,928,044; 3,930,861; 3,930,866 and 3,933,500.

If Q' is not hydrogen but instead a group which is eliminated on reaction with the oxidised developer, the magenta couplers are diequivalent and are described, for example, in U.S. Pat. Nos. 3,006,579, 3,419,391, 3,311,476, 3,432,521, 3,214,437, 4,032,346, 3,701,783, 4,351,897 and 3,227,554, EP-A-133 503, DE-A-2 944 601, JP-A-78/34 044, 74/53 435, 74/53 436, 75/53 372 and 75/122 935.

2-Pyrazolone rings can be linked via a divalent Q', giving bis-couplers, which are described, for example, in U. S. Pat. Nos. 2,632,702; 2,618,864; GB-A-968 461, GB-A-786 859, JP-A-76/37 646, 59/4086, 69/16 110, 69/26 589, 74/37 854 and 74/29 638.

Other types of magenta couplers which can be stabilised particularly well by compounds of the formula (1) are pyrazoloazole magenta couplers, for example pyrazolotetrazoles, described in JP-A-85/33 552; pyrazolopyrazoles, described in JP-A-85/43 695; pyrazoloimidazoles, described in JP-A-85/35 732, JP-A-86/18 949 and US-A-4,500,630; pyrazolotriazoles, described in JP-A-85/186 567, JP-A-86/47 957, JP-A-85/215 687, JP-A-85/197 688, JP-A-85/172 982, EP-A-119 860, EP-A-173 256, EP-A-178 789, EP-A-178 788 and in Research Disclosure 84/24 624.

Other pyrazoloazole magenta couplers are described in: JP-A-86/28 947, JP-A-85/140 241, JP-A-85/262 160, JP-A-85/213 937, EP-A-177 765, EP-A-176 804, EP-A-170 164, EP-A-164 130, EP-A-178 794, DE-A-3 516 996, DE-A-3 508 766 and Research Disclosure 81/20 919, 84/24 531 and 85/25 758.

Pyrazoloazole magenta couplers may be described by the formula

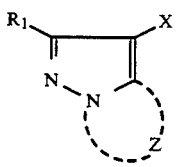

(C)

in which $R_1$ is hydrogen or a substituent, X is hydrogen or a leaving group, and Z is the nonmetallic atoms forming a 5-membered ring containing 2 or 3 nitrogen atoms. These magenta couplers preferably exist in the following structures:

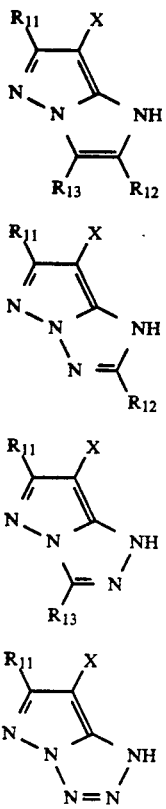

(C-I)

(C-II)

(C-III)

(C-IV)

In these formulae, the substituent $R_{11}$ is, for example, hydrogen, halogen, alkyl, aryl, a heterocyclic group, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, azo, acyloxy, carbamoyloxy, silyloxy, aryloxycarbonylamino, imino, sulfinyl, phosphonyl, aryloxycarbonyl, acyl or azolyl.

A divalent radical $R_{11}$ gives the corresponding bis form.

In particular, $R_{11}$ may be hydrogen, halogen, for example chlorine or bromine; alkyl, for example having 1 to 32 carbon atoms, aralkyl, alkenyl, alkynyl, cycloalkyl or cycloalkenyl and preferably methyl, ethyl, propyl, isopropyl, t-butyl, tridecyl, 2-methanesulfonylethyl, 3-(3-pentadecylphenoxy)propyl, 3-(4-(2-(4-(4-(hydroxyphenylsulfonyl)phenoxy)dodecanamido)-phenyl)propyl, 2-ethoxytridecyl, trifluoromethyl, cyclopentyl, 3-(2,4-di-t-amylphenoxy)propyl; aryl, for example phenyl, 4-t-butylphenyl, 2,4-di-t-amylphenyl or 4-tetradecanamidophenyl; a heterocyclic group, such as 2-furyl, 2-thienyl, 2-pyrimidinyl, or 2-benzothiazolyl; cyano; hydroxyl; nitro; carboxyl; amino; alkoxy, such as methoxy, ethoxy, 2-methoxyethoxy, 2-dodecylethoxy or 2-methanesulfonylethoxy; aryloxy, such as phenoxy, 2-methylphenoxy, 4-t-butylphenoxy, 3-nitrophenoxy, 3-t-butoxycarbamoylphenoxy or 3-methoxycarbamoyl; acylamino, such as acetamido, benzamido, tetradecanamido, 2-(2,4-di-t-amylphenoxy)butanamido, 4-(3-t-butyl-4-hydroxyphenoxy)butanamido or 2-(4-(4-hydroxyphenylsulfonyl)phenoxy)decanamido; alkylamino, such as methylamino, butylamino, dodecylamino, diethylamino or methylbutylamino; anilino, such as phenylamino, 2-chloroanilino, 2-chloro-5-tetradecanaminoanilino, 2-chloro-5-dodecyloxycarbonylanilino, N-acetylanilino or 2-chloro-5-(alpha(3-t-butyl-4-hydroxyphenoxy)dodecanamidoanilino; ureido, such as phenylureido, methylureido or N,N-dibutylureido; sulfamoylamino, such as N,N-dipropylsulfamoylamino or N-methyl-N-decylsulfamoylamino; alkylthio, such as methylthio, octylthio, tetradecylthio, 2-phenoxyethylthio, 3-phenoxypropylthio or 3-(4-t-butylphenoxy)propylthio; arylthio, such as phenylthio, 2-butoxy-5-t-octylphenylthio, 3-pentadecylphenylthio, 2-carboxyphenylthio or 4-tetradecanamidophenylthio; alkoxycarbonylamino, such as methoxycarbonylamino or tetradecyloxycarbonylamino; sulfonamido, such as methanesulfonamido, p-toluenesulfonamido or octadecanesulfonamido; carbamoyl, such as N-ethylcarbamoyl, N,N-dibutylcarbamoyl, N-(2-dodecyloxyethyl)carbamoyl, N-methyl-N-dodecylcarbamoyl or N-(3-(2,4-di-t-amylphenoxy)propyl)carbamoyl; sulfamoyl, such as N-ethylsulfamoyl, N,N-dipropylsulfamoyl, N-(2-dodecyloxyethyl)sulfamoyl, N-ethyl-N-dodecylsulfamoyl, N-ethyl-N-dodecylsulfamoyl or N,N-diethylsulfamoyl; sulfonyl, such as methanesulfonyl, octanesulfonyl, phenylsulfonyl or toluenesulfonyl; alkoxycarbonyl, such as methoxycarbonyl, butoxycarbonyl, dodecyloxycarbonyl or octadecyloxycarbonyl; a heterocyclic group, such as 1-phenyltetrazol-5-oxy or 2-tetrahydropyranyloxy; azo, such as phenylazo, 4-methoxyphenylazo, 4-pivaloylaminophenylazo or 2-hydroxy-4-propanoylphenylazo; acyloxy, such as acetoxy; carbamoyloxy, such as N-methylcarbamoyloxy or N-phenylcarbamoyloxy; silyloxy, such as trimethylsilyloxy or dibutylmethylsilyloxy; aryloxycarbonylamino, such as phenoxycarbonylamino; imido, such as N-succinimido, N-phthalimido or 3-octadecenylsuccinimido; a heterocyclic group, such as benzothiazolylthio, 2,4-diphenoxy-1,3,5-triazole-6-thio or 2-pyridylthio; sulfinyl, such as dodecylsulfinyl, 3-pentadecylphenylsulfinyl or 3-phenoxypropylsulfinyl; phosphonyl, such as phenoxyphosphonyl, octyloxyphosphonyl or phenylphosphonyl; aryloxycarbonyl, such as phenoxycarbonyl; acyl, such as acetyl, 3-phenylpropanoyl, benzoyl or 4-dodecyloxybenzoyl; or azolyl, such as imidazolyl, pyrazolyl or 3-chloropyrazol-1-yl.

Of these, particular preference is given to alkyl, aryl, alkoxy, aryloxy, alkylthio, ureido, urethane and acylamino.

$R_{12}$ can be as defined for $R_{11}$ and is preferably hydrogen, alkyl, aryl, a heterocyclic group, alkoxycarbonyl, carbamoyl, sulfamoyl, sulfinyl, acyl or cyano.

$R_{13}$ is likewise as defined for $R_{11}$ and is preferably hydrogen, alkyl, aryl, a heterocyclic group, alkoxy, aryloxy, alkylthio, arylthio, alkoxycarbonyl, carbamoyl or acyl.

X is hydrogen or a group which is eliminated on reaction with the oxidation product of the developer. Examples of leaving groups of this type are halogen, alkoxy, aryloxy, acyloxy, alkyl- or arylsulfonyloxy, acylamino, alkyl- or arylsulfonamido, alkoxycarbonyloxy, aryloxycarbonyloxy, alkyl- or arylthio, carbamoylamino, imido, arylazo, etc. These groups may be further substituted.

X is preferably halogen, such as fluorine, chlorine or bromine; alkoxy, such as ethoxy, dodecyloxy, methoxyethylcarbamoylmethoxy, carboxypropoxy, methylsulfonylethoxy or ethoxycarbonylmethyoxy; aryloxy, such as 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy; acetyloxy, such as acetoxy, tetradecanoyloxy or benzoyloxy; alkyl- or arylsulfonyloxy, such as methanesulfonyloxy or toluenesulfonyloxy; acylamino, such as dichloroacetylamino or heptafluorobutyrylamino; alkyl- or arylsulfonamido, such as methanesulfonamido, trifluoromethanesulfonamido or p-toluenesulfonamino; alkoxycarbonyloxy, such as ethoxycarbonyloxy or benzyloxycarbonyloxy; aryloxycarbonyloxy, such as phenoxycarbonyloxy; alkyl- or arylthio, such as dodecylthio, 1-carboxydodecylthio; phenylthio, 2-butoxy-5-t-octylphenylthio or tetrazolylthio; carbamoylamino, such as N-methylcarbamoylamino or N-phenylcarbamoylamino; imidazolyl, pyrazolyl, triazolyl, tetrazolyl or 1,2-dihydro-2-oxo-1-pyridyl; imido, such as succinimido or hydantoinyl, or arylazo, such as phenylazo or 4-methoxyphenylazo.

In addition, X may form, for example with the coupler of the formula (C-III), the bis compound of the formula

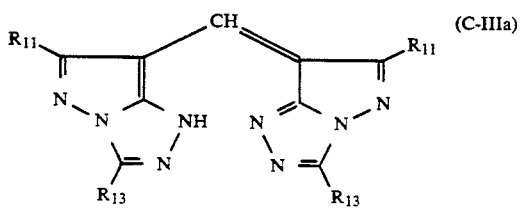
(C-IIIa)

and also corresponding bis compounds with the couplers of the formulae (C-I), (C-II) and (C-IV).

X may also contain photographically active groups, such as development inhibitors or accelerators. However, X is preferably halogen or one of said alkoxy, aryloxy, alkyl or arylthio radicals or is a 5- or 6-membered nitrogen-containing ring which is bonded to the pyrazoloazole system via a nitrogen atom.

Pyrazoloazole couplers are preferably stabilised using the compounds of the formula (1).

The compounds of the formula (1) can be incorporated into layers of photographic materials in a conventional manner. These layers may be pure binder layers, for example gelatin layers, or layers containing silver halide, suitable silver halides being the conventional halides such as chloride, bromide and iodide and mixtures thereof. The layers may also contain other components which are conventional in photographic materials, such as antifogging agents, filter dyes, optical whiteners, UV absorbers and conventional organic stabilisers, such as sterically hindered amines and phenols. Besides magenta couplers, the layers may also contain mixtures of couplers, for example of magenta couplers or magenta, cyan and yellow couplers.

In particular with respect to the stabilisation of magenta image dyes, the use of a combination of compounds of the formula (1) with known light stabilisers of the hydroquinone or, in particular, hydroquinone ether type has proven successful. These compounds are preferably in the same layer as the compounds of the formula (1).

Hydroquinone compounds of this type are described in greater detail in the following patent specifications:
U.S. Pat. Nos. 2,360,290; 2,336,327; 2,403,721; 2,418,613; 2,675,314; 2,701,197; 2,710,801; 2,732,300; 2,728,659; 2,735,765; 2,704,713; 2,937,086; 2,816,028; 3,582,333; 3,637,393; 3,700,453; 3,960,570; 3,935,016; 3,930,866; 4,065,435; 3,982,944; 4,232,114; 4,121,939; 4,175,968; 4,179,293; 3,591,381; 3,573,052; 4,279,990; 4,429,031; 4,346,165; 4,360,589; 4,346,167; 4,385,111; 4,416,978; 4,430,425; 4,277,558; 4,489,155; 4,504,572 and 4,559,297, FR-A-885 982; GB-A-891 158, 1 156 167, 1 363 921, 2 022 274, 2 066 975, 2 071 348, 2 081 463, 2 117 526 and 2 156 091; DE-A-2 408 168, 2 726 283,2 639 930, 2 901 520, 3 308 766, 3 320 483 and 3,323,699; DD-A-216 476,214 468 and 214 469, EP-A-84 290, 110 214, 115 305, 124 915, 124 877, 144 288, 147 747, 178 165 and 161 577; JP-A-75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6652, 86/72 040, 87/11 455 and 87/62 157, and in Research Disclosure 79/17 901, 79/17 905, 79/18 813, 83/22 827 and 84/24 014.

Hydroquinone ethers are described in greater detail in the following patent specifications:
U.S. Pat. Nos. 3,285,937; 3,432,300; 3,519,429; 3,476,772; 3,591,381; 3,573,052; 3,574,627; 3,573,050; 3,698,909; 3,764,337; 3,930,866; 4,113,488; 4,015,990; 4,113,495; 4,120,723; 4,155,765; 4,159,910; 4,178,184; 4,138,259; 4,174,220; 4,148,656; 4,207,111; 4,254,216; 4,314,011; 4,273,864; 4,264,720; 4,279,990; 4,332,886; 4,436,165; 4,360,589; 4,416,978; 4,385,111; 4,459,015; 4,559,297; 4,616,082 and 4 631 252; GB-A 1 347 556, 1 366 441, 1 547 392, 1 557 237 and 2 135 788; DE-A 3 214 567; DD-214 469, EP-A 161 577, 167 762, 164 130 and 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/50 244, 80/52 057, 80/70 840, 80/139 383, 81/30 125, 81/151 936, 82/34 552, 82/68 833, 82/204 036, 82/204 037, 83/134 634, 83/207 039, 84/60 434, 84/101 650, 84/87 450, 84/149 348, 84/182 785, 86/72 040, 87/11 455, 87/62 157, 87/63 149, 86/2151, 86/6652, 86/48 855 and in Research Disclosure 78/17 051.

Examples of particularly suitable light stabilisers which can be used in combination with the compounds of the formula (1) conform to the formulae

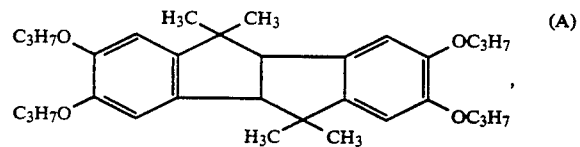
(A)

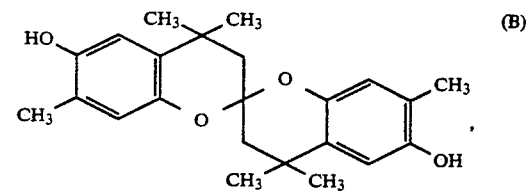
(B)

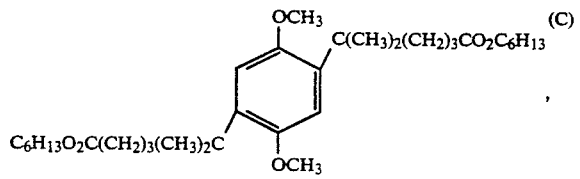
(C)

-continued

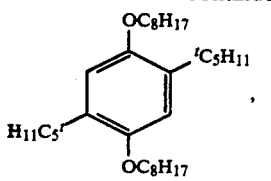

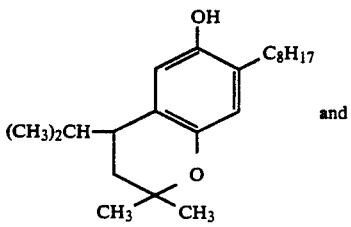    and

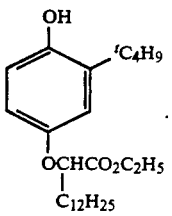

The present invention also relates to the novel compounds of the formula

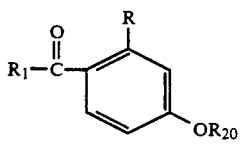    (1a)

in which R is hydrogen or hydroxyl, R₁ is alkyl or alkoxy in each case having 1 to 18 carbon atoms, or —NR₄R₅ in which R₄ and R₅, independently of one another, are hydrogen or alkyl having 1 to 18 carbon atoms, or R₁ is a radical of the formula

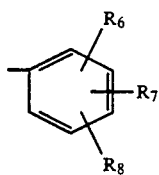

in which R₆, R₇ and R₈, independently of one another, are hydrogen, hydroxyl or alkyl having 1 to 8 carbon atoms, or R₁ is a radical of the formula

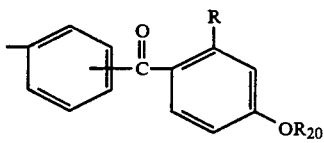

in which R is as defined above, and R₂₀ is a radical of the formula

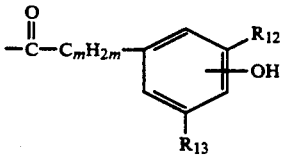    (D)

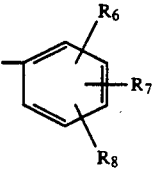    (E)

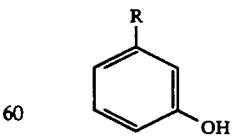    (F)

in which $R_{12}$ and $R_{13}$, independently of one another, are hydrogen, alkyl in each case having 1 to 8 carbon atoms, or cyclopentyl, and m is 1 to 6, or $R_{20}$ is —CO—alkenyl having 2 to 18 carbon atoms in the alkenyl moiety or, if R is hydrogen, —CO—alkyl having 1 to 18 carbon atoms in the alkyl moiety.

Examples of substituents used in the compounds of the formula (1a) are given at the appropriate points in the definitions of the substituents of the compounds of the formula (1).

These compounds of the formula (1a) and in particular those in which $R_{12}$ and $R_{13}$, independently of one another, are hydrogen or alkyl in each case having 1 to 4 carbon atoms, and m is 2, are also highly suitable for stabilising magenta couplers in photographic materials. A further group of particularly preferred stabilisers are the compounds of the formula (1a) in which $R_{20}$ is —CO—alkenyl having 12 to 18 carbon atoms in the alkenyl moiety, and the compounds in which $R_1$ is alkyl or alkoxy in each case having 1 to 4 carbon atoms, or a radical of the formula

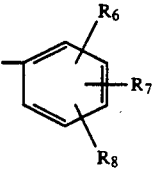

in which $R_6$, $R_7$ and $R_8$, independently of one another, are hydrogen, hydroxyl or alkyl in each case having 1 to 4 carbon atoms. They can be used, in particular, to stabilise magenta couplers of the pyrazoloazole type mentioned above. In combination with the abovementioned light screens of the hydroquinone or hydroquinone ether type, the compounds of the formula (1a) are effective stabilisers for magenta image dyes.

The compounds of the formula (1) and the compounds of the formula (1a) according to the invention can be prepared in a manner known per se. For example, a phenol of the formula

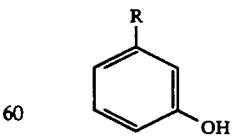

is acylated by Friedel-Crafts acylation using R₁COCl by means of AlCl₃ or ZnCl₂, and the substituent R₃ or R₂₀ is introduced into the molecule by further acylation.

The examples below illustrate the invention in greater detail. Percentages are by weight, unless stated otherwise.

PREPARATION EXAMPLES

Example 1

Preparation of 3,5-di-tert-butyl-2',4,4'-trihydroxybenzophenone 107.5 g of 3,5-di-tert-butyl-4-hydroxybenzoyl chloride and 48.4 g of resorcinol are suspended in 400 ml of nitrobenzene and warmed to 50° C. The brown solution is cooled to 0° C. 58.7 g of aluminium chloride are added in portions over the course of 45 minutes with vigorous stirring. The reaction mixture is slowly warmed to 20° C. over the course of 18 hours. The mixture is subsequently stirred at 50° C. for a further 4 hours, then cooled to room temperature and poured into 500 ml of hydrochloric acid/ice. The thick yellow suspension is extracted with ether, the ether phase is extracted with 500 ml of sodium hydroxide (15%), and the basic solution is washed three times with 250 ml of ether in each case, acidified to a pH of 1–2 using 15% hydrochloric acid and extracted with ether. The ether extracts are combined, dried and evaporated under reduced pressure, giving 124.4 g of 3,5-di-tert-butyl-2',4,4'-trihydroxybenzophenone, which, after recrystallisation from methanol, has a melting point of 192°–193° C.

Example 2

Preparation of the compound of the formula (2)

12.0 g of 3,5-di-tert-butyl-2',4,4'-trihydroxybenzophenone and 3.9 g of triethylamine are dissolved in 20 ml of tetrahydrofuran and 40 ml of toluene. The orange-beige solution is cooled to 0° C. A solution of 11.2 g of 3,5-di-tert-butyl-4-hydroxyphenylpropionyl chloride in 40 ml of toluene is added dropwise at between 0° and 5° C. over the course of 1 hour with vigorous stirring, and the mixture is subsequently stirred at room temperature for 2 days. The reaction mixture is poured into 700 ml of ice-water, and the phases are separated. The aqueous phase is extracted with toluene, and the toluene phases are combined, washed, dried and evaporated under reduced pressure. The beige oil is chromatographed on silica gel and recrystallised from petroleum ether (40°–60° C.)/ethyl acetate, giving 21.0 g of 4'-[3,5-di-tert-butyl-4-hydroxyphenylpropionyloxy]-3,5-di-tert-butyl-2',4-dihydroxybenzophenone of melting point 145°–147° C.

Example 3

The procedure as described in Example 2 is repeated using the corresponding amount of 3,5-di-tert-butyl-4-hydroxybenzoyl chloride, to give 4'-[3,5-di-tert-butyl-4-hydroxybenzoyloxy]-3,5-di-tert-butyl-2',4-dihydroxybenzophenone (compound No 4) of melting point 120°–122° C.

Example 4

The procedure as described in Example 2 is repeated using the corresponding amount of 3-tert-butyl-4-hydroxy-5-isopropylphenylpropionyl chloride, to give 4'-[3-tert-butyl-4-hydroxy-5-isopropylphenylpropionyloxy]-3,5-di-tert-butyl-2',4-dihydroxybenzophenone (compound No. 3) of melting point 154°–157° C.

Example 5

The procedure as described in Example 2 is repeated using the corresponding amount of 3,5-di-tert-butyl-4-hydroxyphenyl-2-methylpropionyl chloride, to give 4'-[3,5-di-tert-butyl-4-hydroxyphenyl-2-methylpropionyloxy]-3,5-di-tert-butyl-2',4-dihydroxybenzophenone (compound No. 5) of melting point 163°–165° C.

Example 6

The procedure as described in Example 2 is repeated using the corresponding amount of acetyl chloride, to give 4-acetoxy-3,5-di-tert-butyl-2',4-dihydroxybenzophenone of melting point 182°–186° C.

Example 7

The procedure as described in Example 2 is repeated using the corresponding amount of 2,4-dihydroxybenzophenone, to give 4'-[3,5-di-tert-butyl-4-hydroxyphenylpropionyloxy]-2'-hydroxybenzophenone (compound No. 18) of melting point 122°–124° C.

Use Examples

Examples 8–17

0.044 g of the magenta coupler of the formula

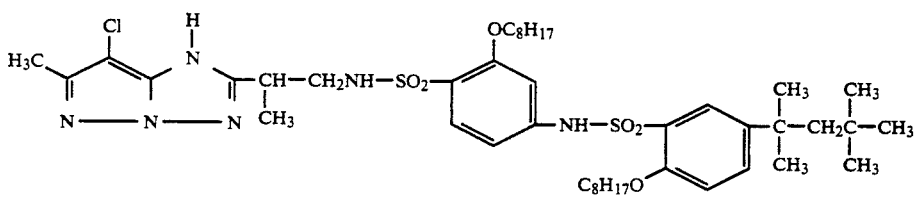

and 0.0155 g of one of the stabilisers listed in the table below are dissolved in 2 ml of a mixture of tricresyl phosphate and ethyl acetate (1.1 g/100 ml).

9.0 ml of a 2.3% aqueous gelatin solution adjusted to a pH of 6.5, and 0.436 g/l of the wetting agent of the formula

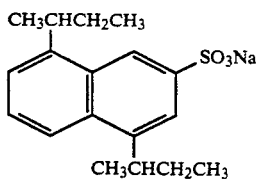

are added to 1.0 ml of this solution. The solution is subsequently emulsified for 3 minutes using ultrasound.

2 ml of a silver bromide emulsion having a silver content of 3 g/l, and 1 ml of a 0.7% aqueous solution of the curing agent of the formula

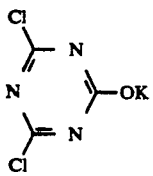

are added to 5 ml of the resultant coupler emulsion. The mixture obtained in this way is cast onto a plastic-coated paper (13×18 cm). After a cure time of 7 days, the sample is exposed behind a step wedge at 125 lux·s and subsequently processed using Ektaprint 2 ® chemicals (Kodak).

The resultant magenta wedge is stored for 28 days in a climatic chamber at 75° C. and a relative atmospheric humidity of 60%. The climatic yellowing, which is a measure of the stability of the photographic images in the dark, is then determined by measuring the $D_{min}$(blue) value (Macbeth TR 924 ® densitometer) before and after the treatment:

Climatic yellowing = $[D_{min}(\text{blue})]_{28} - [D_{min}(\text{blue})]_0$.

As comparison, a sample without stabiliser is subjected to the same conditions. The results are given in the table below.

TABLE 1

| Example | Stabiliser of the Formula | Climatic yellowing |
|---|---|---|
| 8 | none | 0.25 |
| 9 | (2) | 0.16 |
| 10 | (3) | 0.16 |
| 11 | (22) | 0.18 |
| 12 | (23) | 0.16 |
| 13 | (21) | 0.17 |
| 14 | (24) | 0.18 |
| 15 | (28) | 0.18 |
| 16 | (29) | 0.18 |
| 17 | (30) | 0.19 |
| 18 | (27) | 0.13 |
| 19 | (31) | 0.18 |
| 20 | (32) | 0.15 |
| 21 | (33) | 0.16 |
| 22 | (10) | 0.16 |

The stabilisers used according to the invention show good stabilisation of the magenta coupler in the samples used.

Example 23

Magenta wedges are produced as described in Examples 8–22, but with the difference that the 0.0155 g of a stabiliser of the formula (2) is replaced by only 0.0078 g, or by 0.0155 g of the light stabiliser of the formula (A) or by 0,0078 g of (2) and 0,0155 g of (A). These wedges are treated in a climatic chamber as described in Examples 8–22, but are additionally exposed to a 2500 W-Xenon lamp at 30 kJ/cm² behind a UV filter (Kodak 2c) in an Atlas Weather-O-Meter.

The drop in colour density (%) at the absorption maximum of the magenta colour dye which occurs during the treatment is measured using a densitometer (Macbeth TR 924 A) and is shown in the table below. The lower the drop in density, the greater the light screening action.

TABLE 2

| Additional light stabiliser | Stabiliser of the formula | Drop in colour density (%) | Climatic yellowing |
|---|---|---|---|
| — | — | 87 | 0.25 |
| (A) | — | 21 | 0.24 |
| — | (2) | 86 | 0.17 |
| (A) | (2) | 17 | 0.18 |

What is claimed is:

1. A compound of the formula

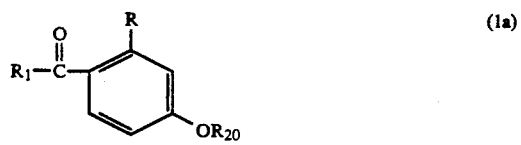

(1a)

in which
R is hydrogen or hydroxyl,
$R_1$ is a radical of the formula

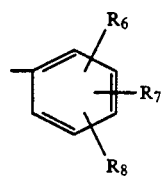

in which
$R_6$ is hydroxyl,
$R_7$, which is ortho to $R_6$, is alkyl having 1 to 8 carbon atoms, and
$R_8$ is hydrogen, hydroxyl or alkyl having 1 to 8 carbon atoms, or
$R_1$ is a radical of the formula

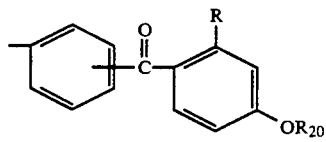

in which R is as defined above, and $R_{20}$ is a radical of the formula

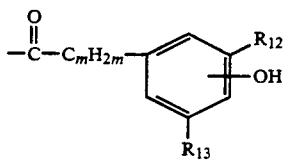

in which
$R_{12}$ is alkyl having 1 to 8 carbon atoms,
$R_{13}$ is hydrogen, alkyl having 1 to 8 carbon atoms, or cyclopentyl, and
m is 1 to 6.

2. A compound according to claim 1 in which
$R_{12}$ is alkyl having 1 to 4 carbon atoms,
$R_{13}$ is hydrogen or alkyl having 1 to 4 carbon atoms, and
m is 2.

3. A compound according to claim 1 in which
$R_1$ is a radical of the formula

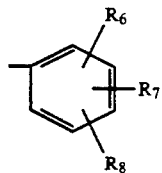
in which
R₆ is hydroxyl,
R₇, which is ortho to R₆, is alkyl having 1 to 4 carbon atoms, and
R₈ is hydrogen, hydroxyl or alkyl having 1 to 4 carbon atoms.
4. The compound according to claim 1, which is 4'-[3,5-di-tert-butyl-4-hydroxyphenylpropionyloxy]-3,5-di-tert-butyl-2',4-dihydroxybenzophenone.
* * * * *